(12) United States Patent
Balsells

(10) Patent No.: US 7,070,455 B2
(45) Date of Patent: Jul. 4, 2006

(54) STACKABLE ASSEMBLY FOR DIRECT CONNECTION BETWEEN A PULSE GENERATOR AND A HUMAN BODY

(75) Inventor: Peter J. Balsells, Newport Beach, CA (US)

(73) Assignee: Bal Seal Engineering Co., Inc., Lake Forset, CA (US)

( * ) Notice: Subject to any disclaimer, the term of this patent is extended or adjusted under 35 U.S.C. 154(b) by 0 days.

(21) Appl. No.: 11/062,168

(22) Filed: Feb. 18, 2005

(65) Prior Publication Data

US 2005/0186829 A1 Aug. 25, 2005

Related U.S. Application Data

(60) Provisional application No. 60/547,279, filed on Feb. 23, 2004.

(51) Int. Cl.
*H01R 24/04* (2006.01)

(52) U.S. Cl. .................. 439/668; 439/909; 607/37

(58) Field of Classification Search ................ 439/668, 439/669, 841, 909; 607/37
See application file for complete search history.

(56) References Cited

U.S. PATENT DOCUMENTS

| 885,864 | A | 4/1908 | Read |
|---|---|---|---|
| 2,902,629 | A | 9/1959 | Little et al. |
| 3,058,083 | A | 10/1962 | Schneider |
| 3,566,192 | A | 2/1971 | Stump |
| 3,569,790 | A | 3/1971 | Jenik |
| 4,052,689 | A | 10/1977 | Smith, Sr. |
| 4,934,366 | A | 6/1990 | Truex et al. |
| 5,012,807 | A | 5/1991 | Stutz, Jr. |
| 5,076,270 | A | 12/1991 | Stutz, Jr. |
| 5,807,144 | A | 9/1998 | Sivard |
| 5,989,077 | A | 11/1999 | Mast et al. |
| 6,238,367 | B1 | 5/2001 | Christiansen et al. |
| 6,321,126 | B1 | 11/2001 | Kuzma |
| 6,775,694 | B1 * | 8/2004 | Fougerat ..................... 709/218 |
| 6,816,745 | B1 | 11/2004 | Brand et al. |
| 6,878,013 | B1 * | 4/2005 | Behan ........................ 439/668 |
| 6,895,276 | B1 * | 5/2005 | Kast et al. .................... 607/37 |
| 2003/0050672 | A1 * | 3/2003 | Dahlberg ..................... 607/37 |

* cited by examiner

*Primary Examiner*—Gary F. Paumen
(74) *Attorney, Agent, or Firm*—Walter A. Hackler

(57) ABSTRACT

A stackable electrical connector assembly includes a plurality of contact housings with each housings having a bore therethrough alignable with adjacent housing bores. The adjacent housings define, in combination, spaced apart radial spring grooves. A plurality of electrically conducting garter springs are disposed in corresponding spring grooves with each spring including a lead extending to an exterior of adjacent housings. A cable having a plurality of wires is provided with each wire attached to a corresponding lead. The housings are modular enabling the contacts to provide a different number of terminal connections.

14 Claims, 3 Drawing Sheets

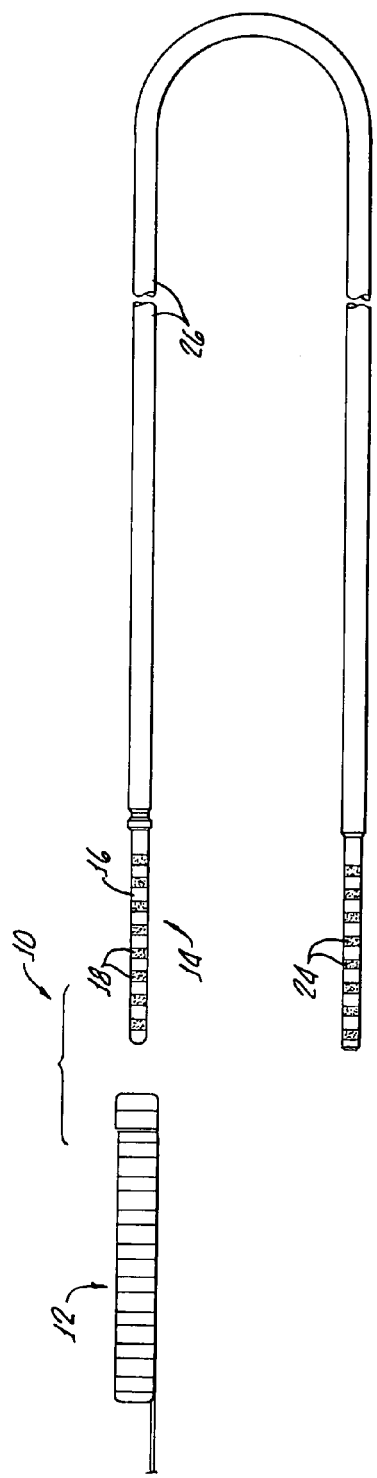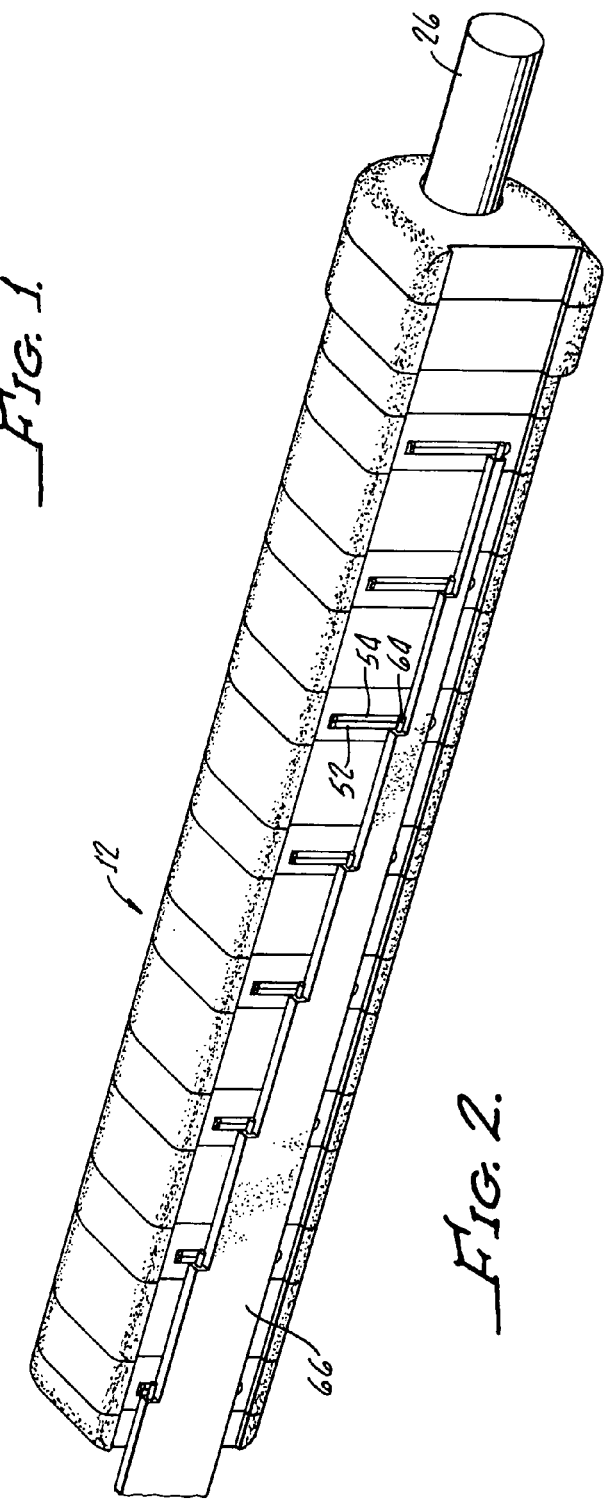

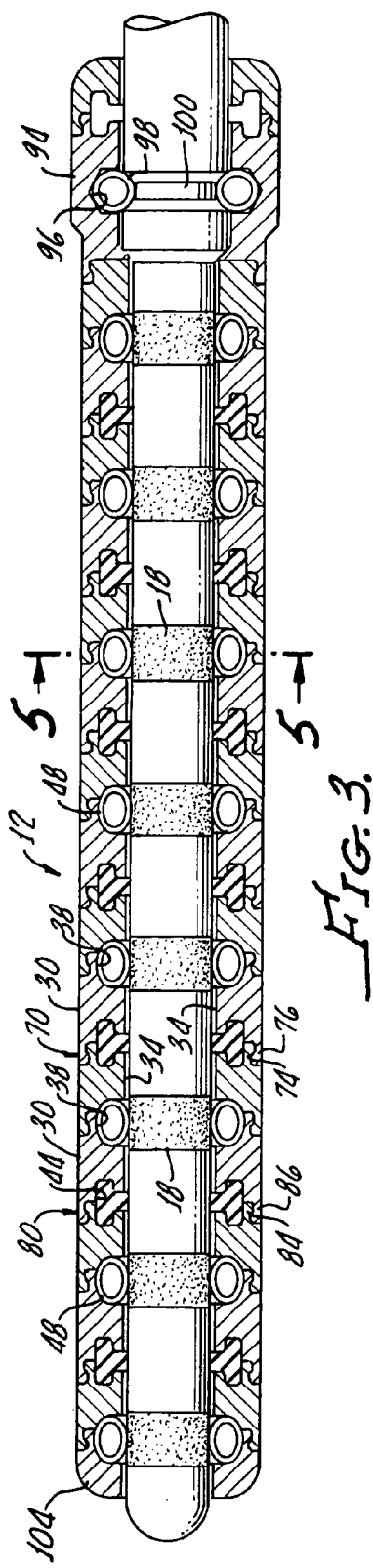
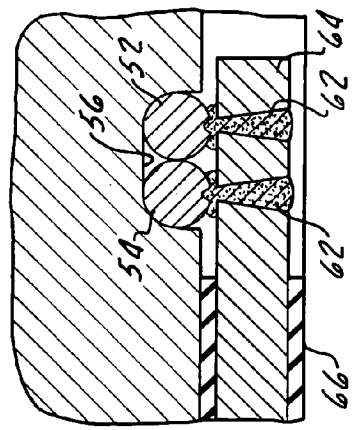
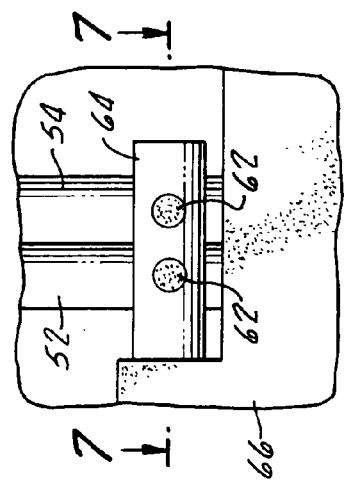
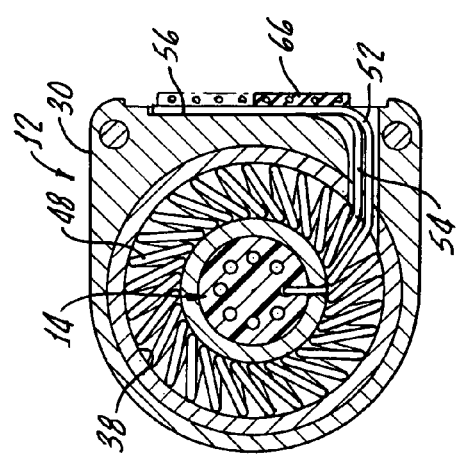

STACKABLE ASSEMBLY FOR DIRECT CONNECTION BETWEEN A PULSE GENERATOR AND A HUMAN BODY

The present application is a continuation of U.S. Ser. No. 60/547,279 filed Feb. 23, 2004, this referenced application is to be incorporated in its entirety into the present application by this specific referenced thereto.

The present invention generally relates to implantable medical electronic devices and electrodes for transferring impulse generator signals to a body such as, for example, pace makers and the like. A lead is typically used with an implant device in order to maintain electrical contact between a desired tissue location and the implanted device. Connection is usually made through the use of a female and male connector.

It is quite necessary that a good electrical contact be maintained throughout the connection and the connection must be secure in order that it maintains consistent conductivity and certainty not disconnect during use. Yet the connection must be easily coupled. In addition, such contacts must remain insulated and sealed from body fluids, which may disrupt conductivity.

Heretofore, connections have utilized springs and metal housings with an electrical signal flowing from a pulse generator through the metal housings and through the springs to a lead from the pulse generator. For the purpose of describing this invention, the word "contact" means a discrete electrical path from a house through a spring to a lead. The word "connector" means an assembly of two or more contacts.

An additional electrical contact has heretofore been required between non-metallic housings and the springs, which results in increased overall resistivity and variation in resistivity of the contact. The present invention is directed to a contact with substantially reduced resistivity and resistivity variability while at the same time maintaining the reliability of a spring contact.

SUMMARY OF THE INVENTION

An electrical connector in accordance with the present invention generally includes a plurality of contact housings with each housing having a bore therethrough which are alignable with adjacent housing bores. This structure provides for a stackable assembly with direct electrical connection between a pulse generator, for example, and a spring contact.

The adjacent housings define, in combination with one another, a plurality of spaced apart radial spring grooves. A plurality of electrically conducting garter springs are provided with each spring being disposed in a corresponding groove.

Each spring includes a lead extending to an exterior of a corresponding housing and a cable is provided having a plurality of wires with each wire attached to a corresponding lead and a direct connection to the pulse generator. In view of the direct connection to the spring, resistivity and resistivity variability of the connector is substantially reduced as hereinafter discussed in greater detail.

More particularly, the connector may include snap fittings removably holding adjacent housings to one another. In this manner, the connector may be assembled, or stacked, with different numbers of individual contacts.

Additionally, adjacent housings may further define, again in combination, seal grooves and the connector may further comprise a plurality of annular seals with each annular seal being disposed in a corresponding seal groove.

These seals provide for sealing between each of the spring grooves within the connector.

In order to reduce resistivity, the lead and the garter spring may be formed from a single piece of wire.

More particularly, the snap fittings may also include overlapping circumferential portions disposed over the seal grooves.

In further combination, the electrical connector in accordance with the present invention may include a receptacle incorporating the contact housings and further include with the plug in turn including a rod receivable by the housing bores with the rod having a plurality of spaced apart electrical contact areas, or terminals, corresponding to the spaced apart spring grooves. In this manner, individual and separate electrical contacts may be established through the use of a single connector in accordance with the present invention.

A latch is provided for removably holding the plug rod in position within the bores, with the snap fittings and seals providing isolation of the contact between the springs and terminals from exterior fluids.

BRIEF DESCRIPTION OF THE DRAWINGS

The present invention may be more clearly appreciated when taken into conjunction with the accompanying drawings in which:

FIG. 1 is a side view of a connector in accordance with the present invention generally showing a receptacle and a plug;

FIG. 2 is an enlarged perspective view of the receptacle shown in FIG. 1 illustrating a plurality of contact housings along with a cable to interconnect to a pulse generator;

FIG. 3 is a cross sectional view of the receptacle shown in FIGS. 1 and 2 more clearly illustrating the receptacle as including a plurality of contact housings, a plurality of springs disposed in grooves and the plug inserted for providing electrical connection therebetween;

FIG. 5 is a cross sectional view taken along the line 5—5 of FIG. 3 more clearly showing one of the garter springs and illustrating leads extending to an exterior of adjacent housing for interconnection with cable wires;

FIG. 6 is an enlarged view of spring lead interconnection with a wire cable;

FIG. 7 is a cross sectional view taken along the line 7—7 of FIG. 6 illustrating the spring leads disposed in a groove and welded to the cable wire;

DETAILED DESCRIPTION

Figure 4:
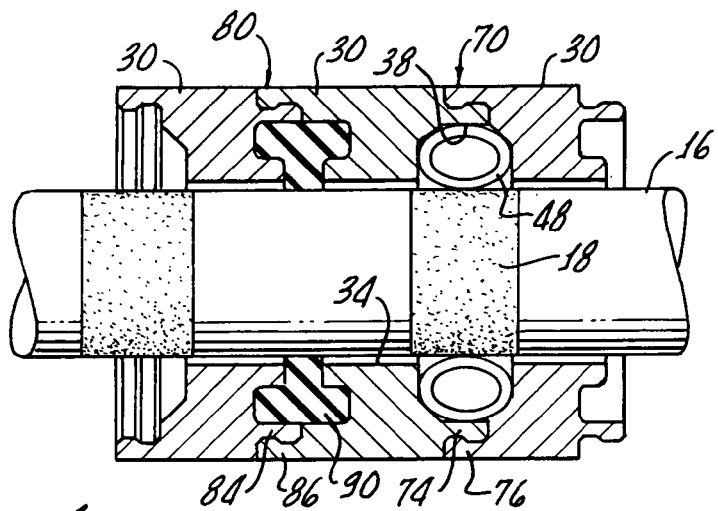
FIG. 4 is an enlarged cross sectional view of a housing in accordance with the present invention generally illustrating a spring groove, a seal groove, and snap fittings.

With reference to FIGS. 1 and 2, there is shown a connector 10 in accordance with the present invention generally including a receptacle 12 and a plug 14. The plug 14 includes a rod 16 having a plurality of spaced apart electrical terminals 18 interconnected to a plurality of electrodes 24 via a wire bundle 26. The electrodes 24 and interconnection to a human body (not shown) are not part of the present invention.

With reference to FIGS. 2 and 3, the connector 12 includes a plurality of modular contact housings 30, each housing having a bore 34 therethrough alignable with adjacent housing bores 34 with the adjacent housing 30 defining, in combination, spaced apart radial spring grooves 38. The modular configuration of the receptacle 12 provides for assembled stacking of a selected number of housings 30.

As illustrated in FIGS. 3 and 4, adjacent housings 30 further define, in combination, seal grooves 44.

With reference also to FIG. 5, the present invention also provides a plurality of electrically conducting garter springs 48 disposed in the corresponding spring grooves 38 with each spring 40 including a lead 52 extending exterior to the housing 30, two leads 52, 54 being shown and nested and a lead groove 56.

It should be appreciated that each spring 48 and leads 52, 54 are formed from a single piece of wire. This is important in that it enables direct connection, 62 by welding or other joining technique to a wire 64 which is part of a cable 66 extending along the exterior of coupled housings 30 forming the receptacle 12 and connecting with the impulse generator. (See also FIG. 2)

This direct connection eliminates one of the conducting elements between a prior art spring (not shown) and a prior art housing (not shown) and accordingly, significantly reduces resistivity between the wire 64 and terminals 18 through the springs 48. That is, only one abutting contact between the spring 48 and terminal 18 occurs, all other connections being through direct connections 62.

With particular reference again to FIGS. 3 and 4, snap fittings 70, which include overlapping circumferential portions 74, 76, removably hold and latch adjacent housings 30 to one another, thus enabling the receptacle 12 to be modularly configured for accepting plugs 14 with different numbers of terminals (not shown).

Accordingly, it should be appreciated that while eight separate interconnections between the connector 10 and the plug 14 are shown in FIGS. 1–3, any number of suitable interconnections may be provided in accordance with the electrical connector of the present invention.

Preferably, the snap fittings 70, including the overlapping circumferential portions 74, 76 are disposed over each one of the spring grooves 38.

Snap fittings 80, including overlapping circumferential portions of 82, 84, may also be provided and centered over the seal groove 44. Accordingly, a ring seal 90 having a T-cross section may be fitting within the seal groove 44 and provide for both radial sealing of the snap fitting 80 as well as axial sealing between the housings 30 and the rod 16 to isolate and seal adjacent spring 48 terminal 18 connections from one another.

With reference to FIG. 3, an end housing 94 includes a groove 96 and spring 98 arrangement which, along with a plug groove 100, removably holds, or latches, the rod 16 in position within the bores 34 with electrical connection between the corresponding rod terminals 18 and springs 48.

Another end housing 104 coupled to the modular housings 30 provides a termination of the connector 12.

Figure 8:
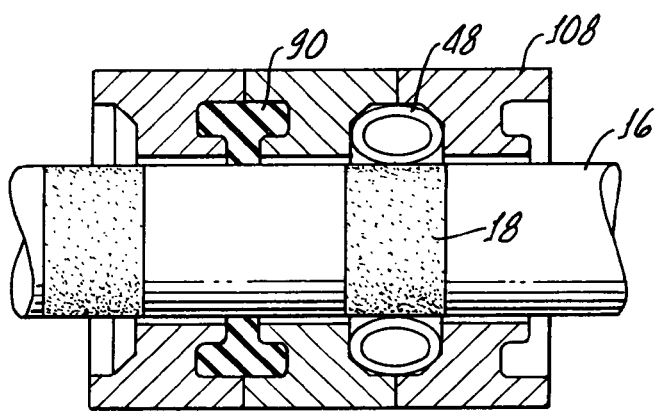
FIG. 8 is a cross sectional view of an alternative embodiment of the present invention not utilizing a snap fittings.

With reference to FIG. 8, there is shown an alternative modular housing 108 arrangement with common reference numbers representing identical or substantially similar structure elements as hereinbefore discussed.

The housings 108 of this embodiment do not include snap fittings but are otherwise clamped together through the use of end fittings, not shown.

Figure 9:
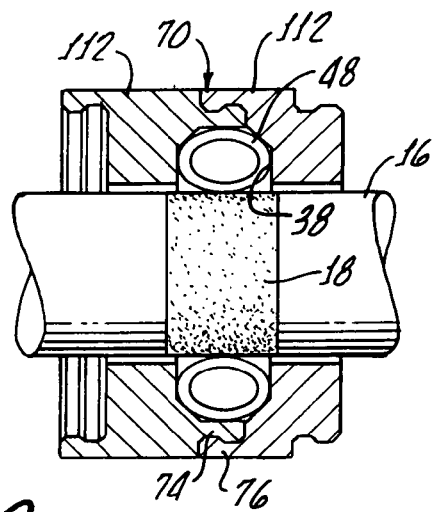
FIG. 9 is a cross sectional view of yet another embodiment of a housing with a spring groove established by adjacent housings and disposed beneath a snap fitting.

FIG. 9 illustrates an embodiment of the present invention substantially similar to hereinabove described in connection with FIGS. 1–7 but including housings 112 without provision for intermediary seals 90, as hereinbefore described.

Although there has been hereinabove described a specific stackable assembly for direct electrical connection between a pulse generator and a human body in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations, or equivalent arrangements which may occur to those skilled in the art, should be considered to be within the scope of the present invention as defined in the appended claims.

What is claimed is:

1. An electrical connector comprising:
a plurality of contact housings, each housing having a bore therethrough alignable with adjacent housing bores, said adjacent housings defining, in combination, spaced apart radial spring grooves;
a plurality of electrically conducting garter springs, each spring disposed in a corresponding groove, each spring including a lead extending to an exterior of the adjacent housings;
a cable having a plurality of wires, each wire attached to a corresponding lead; and
snap fittings removably holding the adjacent housings to each other.

2. The connector according to claim 1 wherein the adjacent housing further define, in combination, seal grooves and the connector further comprises a plurality of annular seals, each annular seal being disposed in a corresponding seal groove.

3. The connector according to claim 1 each spring and lead are formed from a single piece of wire.

4. The connector according to claim 1 wherein each spring includes two leads extending to the exterior of the adjacent housings.

5. The connector according to claim 1 wherein said snap fittings comprise overlapping circumferential portions of each adjacent housings.

6. The connector according to claim 2 further comprising snap fittings, including overlapping circumferential portion of each adjacent housing said snap fittings being disposed over one of the spring groove and seal groove.

7. The connector according to claim 6 wherein each seal groove and annular seal have a T-cross section.

8. An electrical connector comprising:
a receptacle including:
a plurality of contact housings, each housing having a bore therethrough alignable with adjacent housing bores, said adjacent housings defining, in combination, spaced apart radial spring grooves;
a plurality of electrically conducting garter springs, each spring disposed in a corresponding groove, each spring including a lead extending to an exterior of the housings; and
a cable having a plurality of wires, each wire attached to a corresponding lead;

a plug including a rod receivable by the housing bores, said rod having a plurality of spaced apart electrical terminals corresponding to the spaced apart spring grooves;

a latch removably holding the rod in position within the bores with electrical connection between corresponding rod terminals and springs; and snap fittings removably holding the adjacent housings to each other.

9. The connector according to claim 8 wherein the adjacent housing further define, in combination, seal grooves and the connector further comprises a plurality of annular seals, each annular seal being disposed in a corresponding seal groove.

10. The connector according to claim 8 each spring and lead are formed form a single piece of wire.

11. The connector according to claim 8 wherein each spring includes two leads extending to the exterior of the adjacent housings.

12. The connector according to claim 8 wherein said snap fittings comprise overlapping circumferential portions of each adjacent housings.

13. The connector according to claim 9 further comprising snap fittings, including overlapping circumferential portion of each adjacent housing said snap fittings being disposed over one of the spring groove and seal groove.

14. The connector according to claim 13 wherein each seal groove and annular seal house a T-cross section oriented to effect radial sealing with the rod between spring grooves and static axial sealing of a corresponding snap seal.

* * * * *